(12) United States Patent
Inder et al.

(10) Patent No.: US 6,212,949 B1
(45) Date of Patent: Apr. 10, 2001

(54) LEVEL SENSOR AND WASHER UNIT

(75) Inventors: David John Inder; Paul Anthony Higgs; Peter John Le Feuvre, all of Guernsey (GB)

(73) Assignee: Dynex Technologies (Guernsey) Ltd., Guernsey (GB)

( * ) Notice: Subject to any disclaimer, the term of this patent is extended or adjusted under 35 U.S.C. 154(b) by 0 days.

(21) Appl. No.: 09/065,074

(22) PCT Filed: Oct. 28, 1996

(86) PCT No.: PCT/GB96/02627

§ 371 Date: Sep. 1, 1998

§ 102(e) Date: Sep. 1, 1998

(87) PCT Pub. No.: WO97/15809

PCT Pub. Date: May 1, 1997

(Under 37 CFR 1.47)

(30) Foreign Application Priority Data

Oct. 27, 1995 (GB) .................................................. 9522056

(51) Int. Cl.[7] ................................. G01F 23/24; B01L 3/02
(52) U.S. Cl. ...................... 73/304 R; 73/864.11; 73/291; 422/100; 422/106; 422/63
(58) Field of Search ............................. 73/304 R, 290 R, 73/291, 298, 863.01, 863.71, 864.01, 864.11, 866.5; 422/63, 67, 82.02, 100, 106; 338/38; 340/620, 648

(56) References Cited

U.S. PATENT DOCUMENTS

| | | | | |
|---|---|---|---|---|
| 4,803,050 | * | 2/1989 | Mack | 422/65 |
| 5,178,834 | * | 1/1993 | Kagayama et al. | 422/65 |
| 5,736,413 | * | 4/1998 | Uzan et al. | 436/526 |
| 5,897,837 | * | 4/1999 | Mizuno | 422/100 |
| 5,948,359 | * | 9/1999 | Kalra et al. | 422/65 |

* cited by examiner

Primary Examiner—Hezron Williams
Assistant Examiner—Michael Cygan
(74) Attorney, Agent, or Firm—Donald C. Casey, Esq.

(57) ABSTRACT

A fluid level sensor and a washer unit are provided for an automated immonoassay processing system. A washer head (13) is vertically movable by a drive (2) above a reaction tray (8) having fluid (15) in separate cells. The level sensor comprises two electrodes arranged along a fluid path within aspirator tips (6). The electrodes are held at different electrical potentials and are effectively insulated from each other. If fluid is aspirated along the fluid path then the electrodes are bridged. Control means (1) is arranged to detect any change in conductance between the electrodes thereby indicating the presence of fluid (15). The vertical height of the washer head is determined relative to the sample thereby enabling the device to determine the level of the fluid (15).

9 Claims, 5 Drawing Sheets

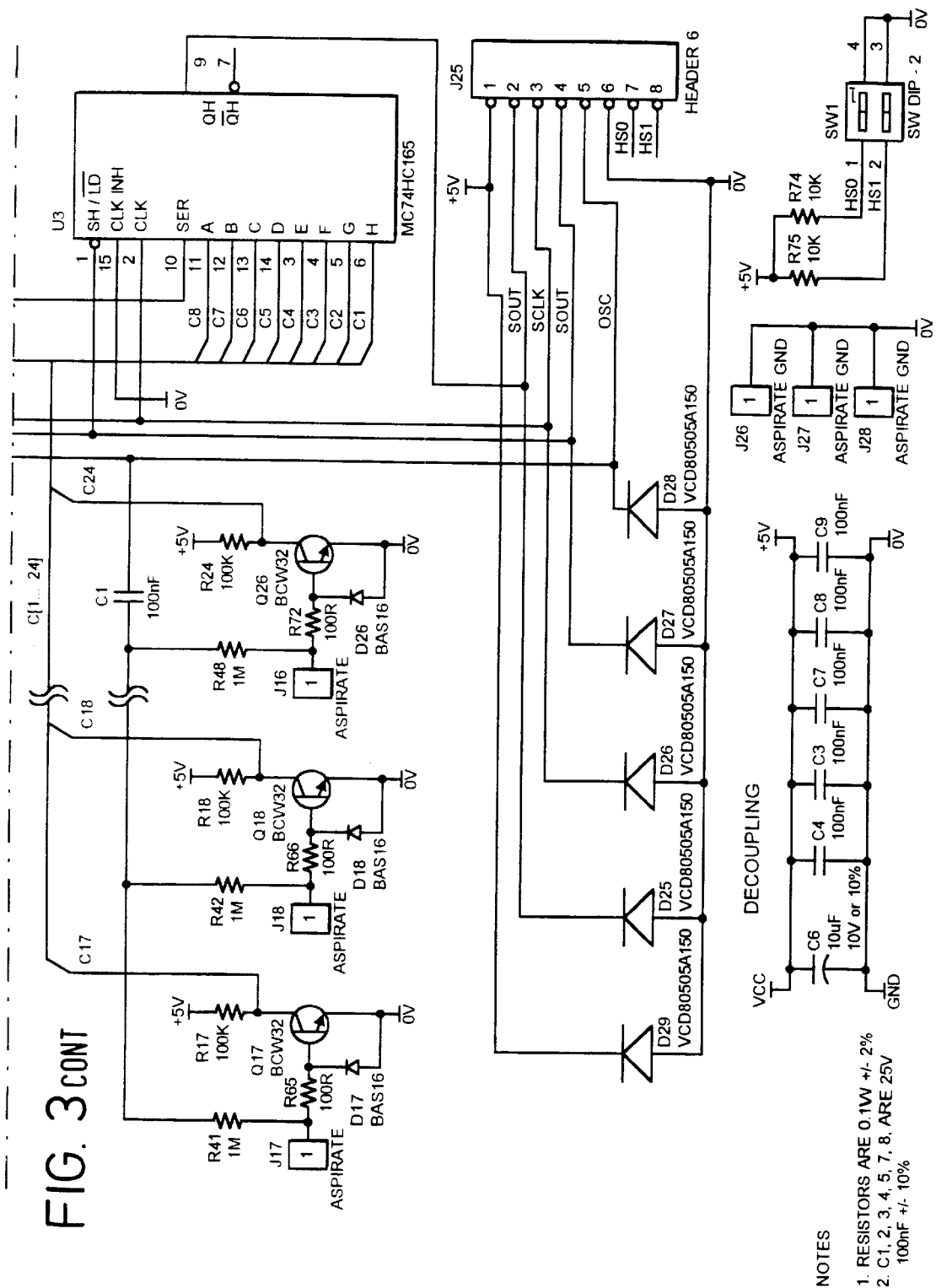

LEVEL SENSOR AND WASHER UNIT

The present invention relates to an automated immunoassay processing system.

When biological, chemical or biochemical products are tested or analysed, these products may be dispensed into cells in reaction trays to enable analysis of the various products to be performed. After a reagent or a plurality of reagents have been dispensed into the cells in the reaction tray, the reagents are then left for a period of time to allow incubation of a biological process or for a chemical reaction or the like to occur.

After this period of time it is necessary to remove the reagent from the cells and wash the cells so that further analysis may be performed. The washing of the cells in the reaction tray is conventionally performed by separate means to the means which dispenses reagent.

After the incubation period, it is desirable to ascertain whether the correct amount of reagent has actually been dispensed into the cells of the reaction tray; otherwise the desired process or reaction may not have occurred. Once the reagent level has been checked, the reagent is aspirated from the cell. It may also be desirable to check that all of the reagent has been removed from the cells before commencing a washing cycle. During the washing cycle it is also desirable to be able to detect whether the correct amount of washing or cleaning fluid has been dispensed into the cells of the reaction trays and to determine whether all the washing fluid has been removed at the end of the washing cycle.

Conventionally apparatus used to clean the cells of a reaction tray, for example after an incubation period, consists of a washer head with a dispensing tip and an aspirate tip corresponding to each cell.

GB-2216260 discloses a device for injecting a fixed quantity of liquid into a reaction tray wherein conductive electrodes are positioned on an injection nozzle and a detecting unit cooperates with the electrodes to detect the surface level of a sample liquid.

U.S. Pat. No. 4,451,433 discloses an automatic chemical reaction analyzer wherein samples are sequentially dispensed into a reaction tray via a first pipetting tube. Reagent solutions are supplied to the reaction trays via a second, conductive, pipetting tube. The liquid levels of the solutions in the reaction trays are detected by a liquid level sensor formed by the second pipetting tube and a conductive electrode.

The object of the present invention is to provide a new and improved automated immunoassay processing system.

According to the present invention there is provided An automated immunoassay processing system including a level sensor, comprising:

a head mounted for vertical movement, said head comprising an aspirate tip having an internal flow passage within and along which first and second electrode means are provided, the electrode means being connected to a detector circuit arranged to give an output signal when the electrode means are bridged by fluid;

aspirating means connected to the aspirate tip;

a motor for moving the head;

a positioning circuit for controlling the motor to position the head at specified vertical positions; and control means connected to receive the output signal of the detector circuit;

characterised in that:

the aspirating means is arranged to aspirate whilst the head is being lowered towards the surface of the fluid;

the first and second electrode means are sequentially positioned so that in use fluid passes through said first electrode means before passing through said second electrode means; and the control means is arranged to produce an indication of the level or volume of fluid in a reaction cell by reference to a vertical position signal when the detector circuit gives an output signal on the aspirate tip coming into contact with fluid in the reaction cell and to generate an output indicating the presence of fluid passing between said first and second electrode means whilst the fluid is being aspirated from the reaction cell.

Various embodiments of the present invention will now be described by way of example only, with reference to the accompanying drawings, in which.

Figure 1:
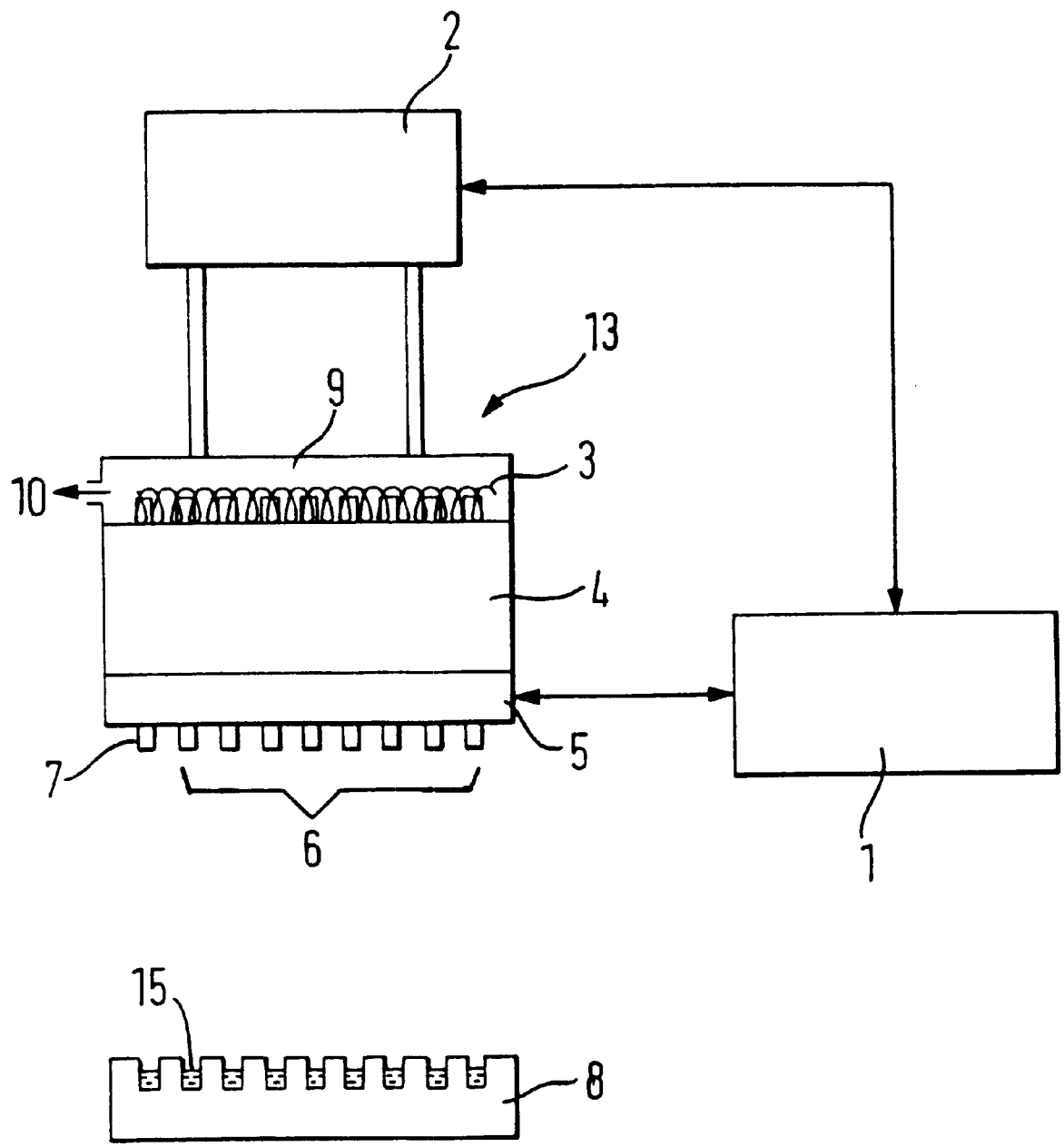
FIG. 1 is a schematic diagram of an automated immunoassay processing system incorporating the invention.

With reference to the drawings, FIG. 1 shows a washer head 13 mounted to be driven vertically up and down by a drive means 2 such as a stepper motor. The drive means 2 is controlled by a control means 1 which may include a program-controlled processor. According to a preferred embodiment a matrix of 8×3 dispense and aspirate tips 6 are positioned on the washer head 13.

The washer head 13 further comprises a printed circuit board (PCB) 5 attached to an insulating block 4. On the upper surface of the insulating block 4 a plenum chamber 9 is provided connected to an aspirate or suction means. An exit passage 10 is provided to allow the removal of fluid drawn along an aspirate fluid path, which includes aspirate tips 6.

Figure 2:
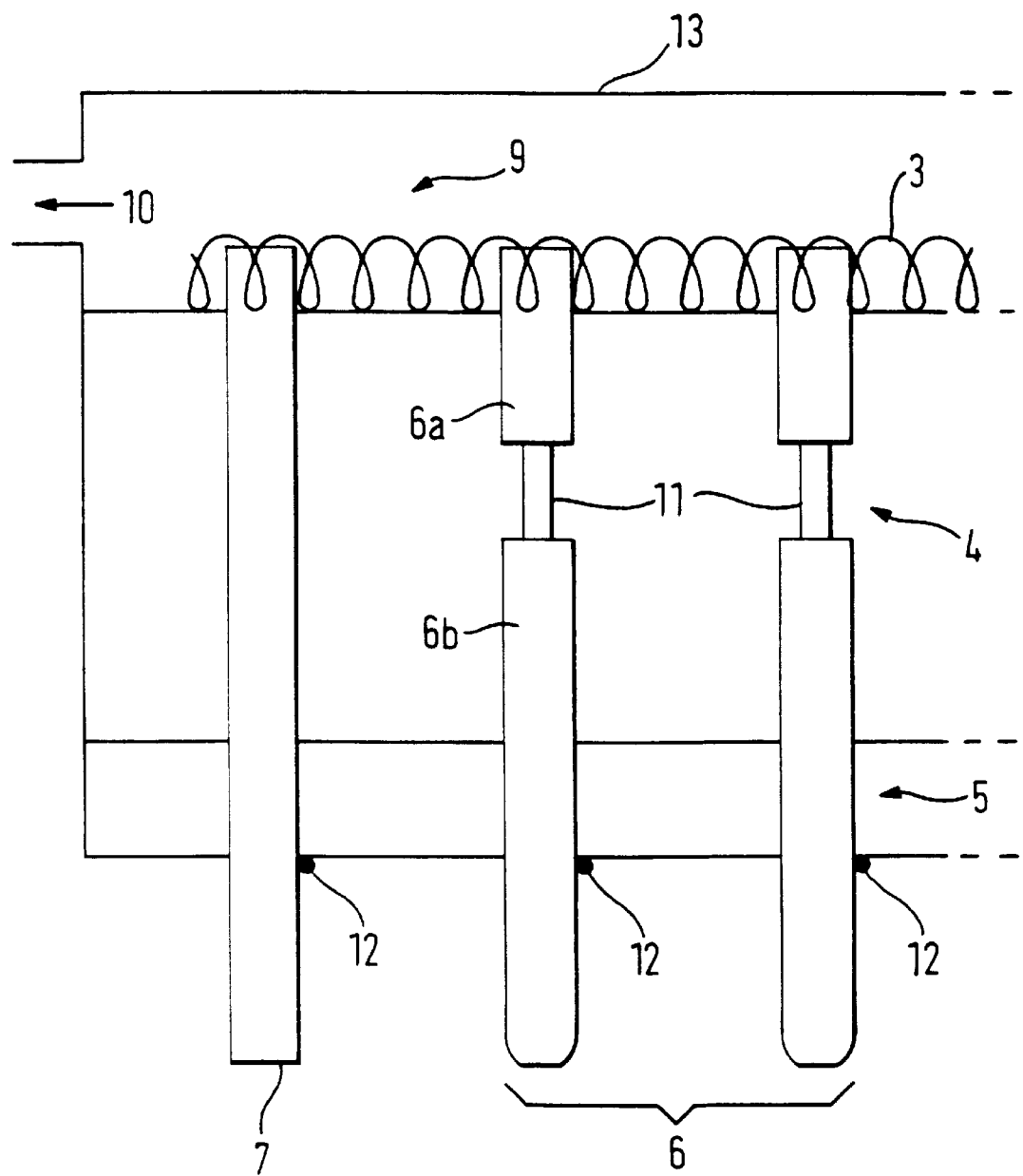
FIG. 2 is a partial section of a washer head of the apparatus of FIG. 1.

The aspirate tips 6 are divided into top and bottom sections 6a and 6b as shown in FIG. 2. Each top section 6a consists of an upper electrode section inserted into a counterbore within the upper surface of the insulating block 4 and each bottom section 6b consists of a lower electrode section inserted into a corresponding counterbore within the lower surface of the insulating block 4. The upper and lower electrode sections consist preferably of stainless steel fabricated in the form of a tube. The external diameter of the counterbores is larger than the central bore 11. For example, the external diameter of the counterbores may be 1.4 mm whereas the central bore 11 is preferably 1.0 mm. The internal diameter of the upper and lower sections of the aspirate tips 6 which are inserted into the two counterbores are typically substantially the same diameter as the internal diameter of the central communicating bore 11. The central communicating bore 11 defines at least a portion of the aspirate fluid path. The depth of the counterbore in the upper surface of the insulating block 4 is typically 20 mm and the depth of the counterbore in the lower surface of the insulating block 4 is typically 30 mm. In use, a reaction tray 8 is vertically spaced below the washer head 13 and the aspirate tips 6.

Preferably, the drive means 2 consists of a stepper motor which can control the vertical displacement of the washer head 13 and aspirate tips 6. According to the preferred embodiment, the stepper motor can control the vertical displacement of the washer head 13 in steps of 0.1 mm. By way of example, the washer head may be lowered at a rate of 75 mms$^{-1}$.

The control means 1 communicates with the PCB 5 of the washer head 13. According to the present invention a fluid or level sensor is provided by arranging two conductive electrode sections, electrically insulated from each other, for example by means of an air gap or other means, along an aspirate fluid path. The air gap is preferably a few millimetres wide. Detector means is connected across the conductive electrode sections to detect the presence of a fluid by detecting a change in conductance between the electrode sections. Since the vertical position of the washer head 13 relative to the reaction tray 8 may be known or determined, for example by the control means 1 and/or the drive means 2, then the sensor may function as a level sensor.

The upper section 6a of the aspirate tip 6 is held, in use, at substantially zero electrical potential. Preferably, zero potential supply means is provided by a rod or tube 7 inserted through a hole or bore axially disposed through the insulating block 4 and through the PCB 5. The top portion of the tube 7 is electrically connected to the top sections of the other aspirate tips 6 in the chamber 9 by means of a connecting means 3. Preferably, the connecting means consists of a metal spring or the like. On the under surface of the PCB 5 the tube 7 is electrically connected to the PCB by an electrical connection 12, for example conductive glue or resin. The lower sections of the aspirate tip 6 also pass through the PCB 5 and are similarly connected to appropriate tracks on the underside of the PCB 5 by means of electrical connections 12. The electrical connections 12 to the aspirate tips 6 are connected according to the preferred embodiment to connectors J1–24 as shown in the circuit diagram in FIG. 3.

The end of the lower section of the aspirate tip 6 may be chamfered, for example by a laser, to form a more defined tip portion. The end of the aspirate tip 6 may also be formed into the shape of a needle.

The electrical connections and components on the PCB 5 are positioned on the lower surface of the PCB 5. Preferably, a single zero potential supply means 7 is provided per row of aspirate tips 6. Therefore according to the preferred embodiment (a matrix of 3×8 aspirate and dispense tips) three zero potential supply means 7 are provided.

An electrical circuit thus connected to the upper and lower sections of the aspirate tips 6 measures the conductance between the upper and lower sections of the aspirate tip 6. The circuit generates an output indicating the presence of fluid passing between the two sections of the tip 6 by detecting the change in conductance between the two sections of the aspirate tip 6. Normally most reagents and washing fluids are aqueous based ionic solutions and can be detected according to the present invention.

Figure 3:
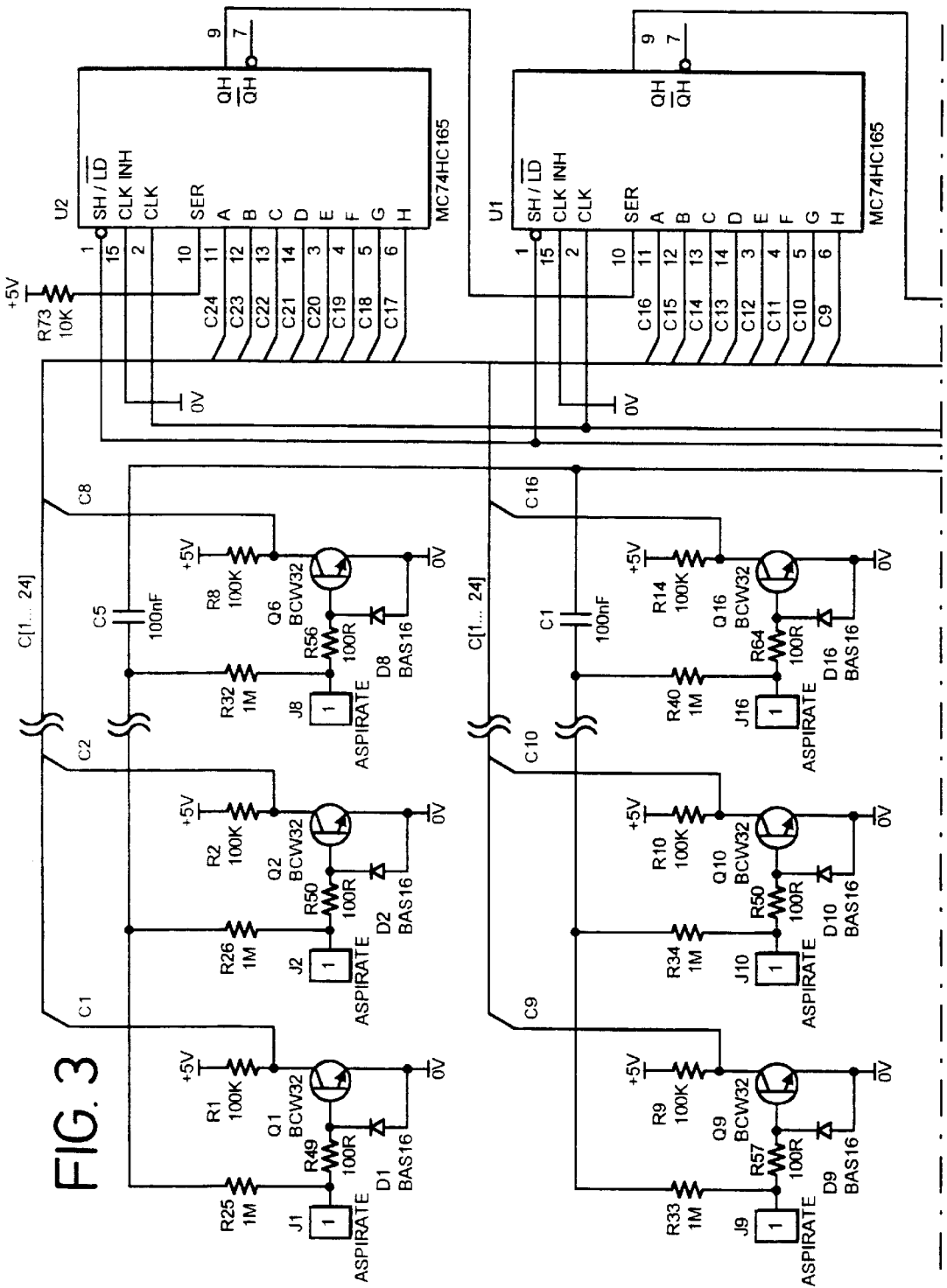
FIG. 3 is a circuit diagram of part of the detector system of a plurality of washer tips.

FIG. 3 is a circuit diagram of part of the detector circuit of a conductive washer head 13. According to the preferred embodiment twenty four aspirate tips are connected to the PCB 5 by means of electrical connections 12. However, according to other embodiments of the present invention a different number of aspirate tips may be used. For example, 8, 16, 32 or 64 aspirate tips 6 may be used as desired.

Pin 7 (HSO) and Pin 8 (HS1) of connector J25 are set to determine which model of apparatus (namely the number of aspirate tips) is being used. Pin 1 is supplied with +5V and pin 6 with 0V from the control means 1. Pin 2 provides shift out, and pin 3 receives a shift clock. Pin 4 receives shift load and pin 5 the oscillator OSC signal. The period of the oscillator is set at 1–2 ms. This is significantly slower than that of the clock period, but is set at such a value due to delays in measuring the presence of fluid because of polarisation effects in the aspirate tip 6. The clock input pulses have a period of substantially 1 $\mu$s and the load input pulse has substantially a similar period. On every load pulse the outputs from each of the fluid sensors are stored in shift registers U1–3. The states of the twenty-four fluid sensors of the preferred embodiment are then cleared from the shift registers U1–3 after twenty-four consecutive clock pulses.

When the top and bottom sections of an aspirate tip 6 are substantially insulated from each other, due to the absence of, for example, reagent or wash fluid (or other aqueous based ionic solution) flowing along the aspirate fluid path, then the output from the transistors Q1–24 connected to the bottom sections of the aspirate tips 6 will be the inverse of the drive signal OSC. The outputs from the transistors Q1–24 are communicated to the shift registers U1–3 via data-buses C[1 . . 24]. In the presence of a fluid flowing along the aspirate fluid path (thereby connecting the top and bottom sections of the aspirate tip 6) the transistor will be held off and the output will remain high.

Figure 4:
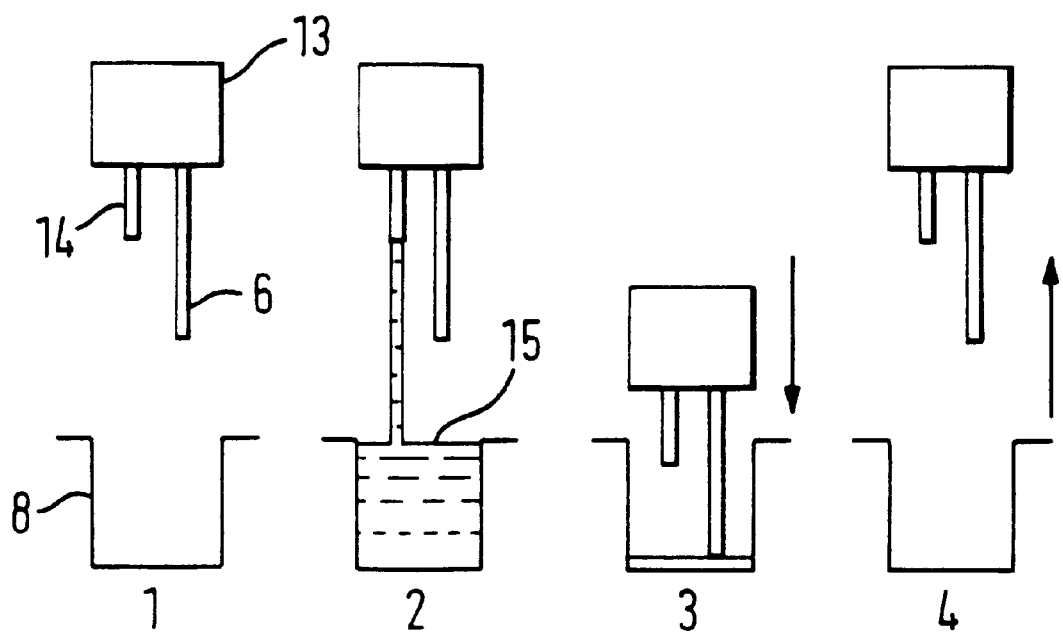
FIG. 4 shows the steps in a normal wash cycle.

FIG. 4 shows some of the steps in a normal wash cycle. Washer head 13 is provided with pairs of dispense tips 14 and aspirate tips 6. The washer head 13 can be moved up and down by means of the mechanical positioning device or drive means 2. The drive means 2 is used to position the vertical height of the dispense 14 and aspirate 6 tips as desired during the various stages of a wash cycle.

A normal wash cycle comprises the steps of firstly positioning the washer head 13 above a sample or container 8, for example a cell of a reaction tray. The required volume of wash fluid 15 is then dispensed into the container 8 positioned below the dispense tip 14 as shown in step 2. The head 13 and the attached tips 6, 14, are then lowered towards the sample or container 8. Preferably, the aspirate tip 6 is longer in length than the dispense tip 14. A suction or aspirate means is activated whilst the washer head 13 is lowered to remove the fluid 15 from the container 8 via the aspirate tip 6. When the detector indicates that fluid has been sensed, the control means 1 can confirm that the liquid level was correct. As the fluid 15 is being removed by the suction or aspirate means the washer head 13 is progressively lowered by drive means 2. The level sensor according to the present invention can determine the level of fluid 15 dispensed into the container 8 and also check that when the aspirate tip is lowered all the way to the bottom of the container all of the fluid has been removed. Finally, the washer head 13 and the dispense 14 and aspirate 6 tips are raised clear from the sample or container 8 as shown in step 4 allowing the next step in the processing system to be performed.

Figure 5:
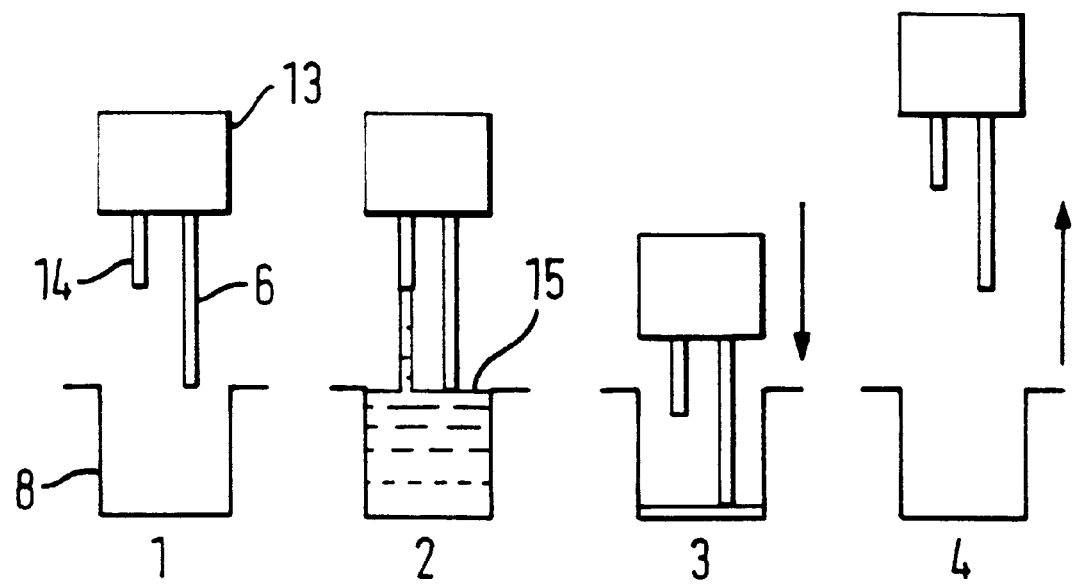
FIG. 5 shows the steps in a top wash cycle.

A second type of wash cycle may alternatively or additionally be performed, known as a top wash cycle. This is shown in FIG. 5. A top wash cycle comprises the steps of firstly positioning the washer head 13 above the container 8 in a similar manner to a normal wash cycle. The washer head 13 is then positioned such that the aspirate tip 6 is set at a level wherein fluid 15 can be aspirated from the container 8 at the same time as fluid 15 is being dispensed from the dispense tip 14 into the container 8. A required quantity of fluid 15 is then dispensed and during this step some of the fluid 15 is aspirated by the aspirate tip 6. When the required sample of fluid 15 has been dispensed the washer head 13 is then lowered by the mechanical positioning means or drive means 2 and the remaining fluid 15 is removed by the aspirate tip 6. Following the removal of any remaining fluid 15 the washer head 13 can be raised clear of the sample 8 (in a similar manner to a normal wash cycle).

During a top wash cycle, the control means 1 can detect the time at which the level sensor detects the presence of fluid IS flowing along the aspirate path of the aspirate tip 6. The control means 1 can then correlate that the dispense flow rate of fluid from the dispense tip 14 was correct. Towards the end of the third stage of the top or normal wash cycle, the level sensor can determine whether all the fluid 15 has been aspirated from the container 8 before proceeding to the next step wherein the head 13 is raised clear from the sample 8.

In both the normal and top wash cycles a validation step may preferably be performed before any wash fluid is dispensed. The validation step ensures that enough reagent was initially dispensed into the container 8, for example during a sample preparation or incubation stage. This is a separate step to those steps performed during a normal or top wash cycle. The validation step comprises positioning the washer head 13 above the container 8 and then lowering the washer head 13 by the mechanical positioning device or drive means 2. The aspirate tip 6 aspirates whilst the washer head 13 is being lowered. The control means 1 can determine the fluid level and thus whether sufficient reagent or fluid was initially dispensed into the container 8. If the detected fluid level indicates that an insufficient amount of reagent or other fluid was dispensed then an error message may be generated by the control means 1 and the results of that cell can be ignored.

According to the present invention, during a normal wash cycle a validation step may be performed after the wash fluid 15 has been dispensed into the container 8 but before the wash fluid 15 is aspirated out of container 8. The validation step checks that the correct amount of wash fluid 15 has been dispensed into the container 8. The level sensor is able to determine whether it is necessary for a further amount of wash fluid 15 to be dispensed by the dispense tip 14. Alternatively or additionally, an error signal may be generated by the control means 1.

Preferably, the container or reaction tray 8 may be such as to allow the volume of fluid contained therein to be determined by measuring the height or depth of the fluid. For example in the field of Microtiter (RTM) technology a depth of 1 mm corresponds to about 28 $\mu$l. The fluid sensor may thus be sensitive to the detection of amounts of about 10 $\mu$l of fluid with 0.1 mm steps of the drive means.

The term "conductance" has been used above in its sense of inverse resistance. However, it would be possible to detect variations in impedance more generally, and in particular a change in capacitance between the electrodes, or a change in combined resistance and capacitance. For measuring capacitance it may be preferable to apply an a.c. signal to the electrodes and to insulate the electrodes on their inside surfaces if it is desired to exclude resistive effects through the fluid.

The above are only specific examples of the invention, and various modifications and embodiments of the invention are also within the scope of the invention which is defined by the claims.

What is claimed is:

1. An automated immunoassay processing system including a level sensor, comprising:

a head mounted for vertical movement, said head comprising an aspirate tip having an internal flow passage within and along which first and second electrode means are provided, each forming a part of the flow passage and being connected to a detector circuit arranged to give an output signal when the electrode means are bridged by fluid;

aspirating means connected to the aspirate tip;

a motor for moving the head;

a positioning circuit for controlling the motor to position the head at specified vertical positions; and control means connected to receive the output signal of the detector circuit;

characterized in that:

the aspirating means is arranged to aspirate while the head is being lowered towards the surface of the fluid;

the first and second electrode means are insulated from each other and vertically positioned so that in use fluid passes through said first electrode means before passing through said second electrode means; and the control means is arranged to produce an indication of the level or volume of fluid in a reaction cell by reference to a vertical position signal when the detector circuit gives an output signal on the aspirate tip coming into contract with fluid in the reaction cell and to generate an output indicating the presence of fluid passing between said first and second electrode means while the fluid is being aspirated from the reaction cell.

2. An automated immunoassay processing system as claimed in claim 1, wherein the control means comprises a processor arranged to produce vertical position signals for controlling the motor in accordance with a stored program.

3. An automated immunoassay processing system as claimed in claim 1, wherein the electrode means comprise two axially spaced metal tubes.

4. An automated immunoassay processing system as claimed in claim 3, wherein the metal tubes are mounted in an insulating block having a through passage which has a narrower-diameter axially-central portion providing two shoulders against which the tubes abut.

5. An automated immunoassay processing system as claimed in claim 1, wherein the head further comprises a dispensing tip for dispensing washing fluid into a reaction cell.

6. An automated immunoassay processing system including a level sensor, comprising:

a head mounted for vertical movement, said head comprising an aspirate tip having an internal flow passage within and along which first and second electrode means are provided, the electrode means being connected to a detector circuit arranged to give an output signal when the electrode means are bridged by fluid;

aspirating means circuit for controlling the motor to position the head at specified vertical positions; and control means connected to receive the output signal of the detector circuit;

characterized in that:

the aspirating means is arranged to aspirate while the head is being lowered towards the surface of the fluid;

the first and second electrode means are sequentially positioned so that in use fluid passes through said first electrode means before passing through said second electrode means; and the control means is arranged to produce an indication of the level or volume of fluid in a reaction cell by reference to a vertical position signal when the detector circuit gives an output signal on the aspirate tip coming into contract with fluid in the reaction cell and to generate an output indicating the presence of fluid passing between said first and second electrode means while the fluid is being aspirated from the reaction cell, said head further comprising a:

dispensing tip arranged to dispense washing fluid into a reaction cell with both the dispensing and aspirate tips positioned above the cell, and wherein after the washing fluid is dispensed the aspirate tip is lowered while aspirating, the control means being arranged to produce an indication of the level of washing fluid when the aspirate tip reaches the fluid surface, whereby the dispensing of a correct quantity of washing fluid may be confirmed.

7. An automated immunoassay processing system as claimed in claim 6, wherein the aspirate tip is arranged to be positioned within the reaction cell and to aspirate while washing fluid is being dispensed from the dispense tip, the control means being arranged to time the period between commencement of dispensing and detection of fluid by the detector circuit when the fluid level reaches the aspirate tip, to confirm that the fluid is being dispensed at an acceptable rate.

8. An automated immunoassay processing system as claimed in claim 6, wherein before a wash cycle, the head is lowered while aspirating and the control means produces an indication of the level of a reagent previously dispensed, so that samples having insufficient reagent can be rejected.

9. A method of sensing a level of fluid in a reaction cell of an automated immunoassay processing system comprising a head, first and second electrode means said electrode means being vertically spaced apart, and an aspirate tip comprising the steps of:

lowering the head towards the reactions cell while generating a vertical position signal of said head relative to said cell;

aspirating while lowering the head;

outputting a signal from each of said electrode means when the first and second electrode means are bridged by fluid passing through said electrode means and aspirate tip;

producing an indication of the level of fluid in the reaction cell by reference to a vertical position signal when the aspirate tip comes into contract with fluid in the reaction cell; and generating an output indicating presence of fluid passing between the first and second electrode means while the fluid is being aspirated from the reaction cell.

* * * * *